US00PP07860P

United States Patent [19]

Reisch et al.

[11] Patent Number: Plant 7,860

[45] Date of Patent: May 5, 1992

[54] GRAPEVINE, 'CHARDONEL'

[75] Inventors: Bruce I. Reisch; Robert M. Pool, both of Geneva; John Einset, deceased, late of Geneva, all of N.Y., by Hjördis Einset, executrix

[73] Assignee: Cornell Research Foundation, Inc., Ithaca, N.Y.

[21] Appl. No.: 585,836

[22] Filed: Sep. 19, 1990

[51] Int. Cl.[5] ..... A01H 5/00

[52] U.S. Cl. ..... Plt./47

[58] Field of Search ..... Plt. 47

[56] References Cited

PUBLICATIONS

New York's Food and Life Sciences Bulletin, Reisch, B. I. et al., No. 132, 1990, pp. 1-3.

Cultivar & Germplasm Releases, Reisch, B. I. et al., HortScience vol. 25(12): 1666-1667, 1990.

Great Lakes Fruit Grower News, Feb., 1985.

*Primary Examiner*—James R. Feyrer

*Attorney, Agent, or Firm*—Jones, Tullar & Cooper

[57] ABSTRACT

A new and distinct variety of grapevine, 'Chardonel', from a cross of 'Seyval' and 'Chardonnay', which can be distinguished by its outstanding wine combined with high productivity, and cold hardiness superior to its acclaimed parent, 'Chardonnay'.

3 Drawing Sheets

BRIEF DESCRIPTION OF THE INVENTION

The invention is a new and distinct variety of grapevine, 'Chardonel', from a cross of 'Seyval' and 'Chardonnay', which can be distinguished by its outstanding wine combined with high productivity, and cold hardiness superior to its acclaimed parent, 'Chardonnay'.

ORIGIN

'Chardonel' was developed by a breeding program of The Department of Horticultural Sciences, Cornell University, New York State Agricultural Experiment Station, Geneva, N.Y. 'Chardonel' resulted from the cross of 'Seyval' with 'Chardonnay'. The cross was made in 1953. Fruit were first observed in 1958 and the original vine was propagated in 1960. Propagation was accomplished by taking hardwood cuttings from the original seedling vine. The cuttings were rooted in a standard potting soil mix in a greenhouse. Rooted cuttings in pots were transferred to an irrigated nursery for one season, dug and stored in a cold room over the winter and planted to a permanent vineyard location as bare-rooted vines the following year. 'Chardonel' had been known previously as GW 9 (Geneva White number 9) and N.Y. 45010.

DESCRIPTION OF THE INVENTION

Own-rooted vines grown in phylloxera (*Daktulosphaira vitifoliae* Fitch.) infested soils are productive and moderately vigorous. Annual cane pruning weights averaged 0.79 kg per vine over a 5 year period in a replicated trial in Dresden, N.Y. (Table 1). This compared favorably to 'Cayuga White' and other varieties in that trial. Vines are more vigorous in Arkansas and Michigan. Five year yield averaged 11.6 t/ha at Dresden, about the same as 'Cayuga White' (Table 1). In Michigan and Arkansas, 'Chardonel' is more productive than 'Cayuga White'. At Geneva, vines of 'Chardonel' have averaged 10.7 t/ha (1987-1989).

TABLE 1

Viticultural production data for 'Cayuga White' and 'Chardonel' grown at three locations.

| Cultivar | Cane Pruning Weight (kg/vine) NY[z] | MI[y] | AR[x] |
|---|---|---|---|
| Cayuga White | 0.71a[w] | 0.50 | 0.60 |
| Chardonel | 0.79a | 1.4-1.8 | 3.00 |

| Cultivar | Clusters Per Vine NY | MI | AR | Yield (t/ha) NY | MI | AR |
|---|---|---|---|---|---|---|
| Cayuga White | 44.0a | | 89.7 | 11.9a | 6.7 | 22.7 |
| Chardonel | 40.2a | | 69.8 | 11.6a | 15.9 | 18.8 |

[z]New York data - pruning weights, cluster numbers and yield based on five years in a replicated trial of 22 white wine cultivars.

[y]Michigan data - collected at the Sodus Horticultural Experiment Station, Michigan. 'Cayuga White' data was collected 1983-1985 (inclusive). 'Chardonel' data was collected 1983-1988 (inclusive).

[x]Arkansas data - based on two years (1986-1987), at Fayetteville, Arkansas.

[w]Means within columns followed by the same letter are not significantly different at $p < 0.05$ according to Duncan's Multiple Range Test. Statistics are presented only where they could be calculated from the available data.

The vines are moderately winter hardy at Geneva and trunk injury is occasionally a problem. However, 'Chardonel' is considerably hardier than 'Chardonnay' and nearly as winter hardy as its 'Seyval' parent. In Michigan, it is rated as hardier than 'Seyval' and 'Vidal blanc'. In 1981, following extensive winter cold damage at Geneva, vines of 'Chardonel' had 74% shootless nodes, comparable with 'Cayuga White' (74%) and 'Vidal blanc' (77%), but worse than 'Aurore' (30%), 'Catawba' (39%), 'Horizon' (49%) and 'Concord' (28%. Trunks of 'Chardonel' are susceptible to damage from low temperatures which may cause damage such as trunk splitting or provoke crown gall disease. After 8 years at Dresden, N.Y., under commercial practices suitable for growing interspecific hybird grapes, 73% of 15 ) winter tender) 'White Riesling' vines were defunct and 7% had trunk damage, while 7% of 'Chardonel' vines had trunk damage and 7% were dead. Vines of 'Cayuga White', 'Horizon', 'Aurore' and 'Concord' had no trunk damage while 7% of 15 vines of 'Vidal blanc' had trunk damage.

Flower of 'Chardonel' are perfect and self-fertile with medium late bloom following late bud-break. Clusters are shouldered and medium-large (200 g), averaging 1.6 clusters per shoot. Very little crop is borne on lateral shoots and cluster thinning is required only infrequently. The amber berries are medium sized and spherical.

'Chardonel' ripens between Oct. 1st and Oct. 15th in New York and Michigan. Juice soluble solids and titratable acidity are usually higher than for 'Cayuga White' (Table 2).

TABLE 2

Juice soluble solids and wine pH and acidity for 'Chardonel' and 'Cayuga White' grown at three locations.

| | Soluble Solids (%) | | | pH | |
|---|---|---|---|---|---|
| Cultivar | NY | MI | AR | NY | MI |
| Cayuga White | 18.9 | 17.3 | 16.6 | 3.26 | 3.04 |
| Chardonel | 19.6 | 20.8 | 21.4 | 2.97 | 3.12 |

| | Titratable Acidity (g/liter) | | | |
|---|---|---|---|---|
| Cultivar | AR | NY | MI | AR |
| Cayuga White | 3.39 | 7.9 | 7.9 | 6.1 |
| Chardonel | 3.43 | 11.7 | 10.6 | 5.3 |

[2]New York data for 'Chardonel' - Soluble solids data based on 11 years (1976-1988, except 1977, 1984); pH data based on 5 years (1982-1983, 1985, 1987-1988); total acidity based on 9 years (1976, 1978-1982, 1986-1988). Wine data for 'Cayuga White' - Soluble solids data based on 10 years (1975-1983 and 1986); pH data based on 2 years (1982-1983); total acidity based on 7 years (1976-1977, 1979-1982 and 1986).

[3]Michigan data - collected at the Sodus Horticultural Experiment Station, Michigan. 'Cayuga White' data was collected 1983-1985 (inclusive). 'Chardonel' data was collected 1983-1988 (inclusive).

[4]Arkansas data - based on two years (1986 and 1987), for 'Cayuga White' and four years (1986-1989) for 'Chardonel'.

Wines, which were first made in 1966, have been described as pleasant and delicate with light fruitiness. In some years, the wine is slightly grassy. The wine has good body and very little of the flavor characteristics of interspecific hybrid grapes. 'Chardonel', when harvested at the appropriate stage, may have potential for sparkling wine production because it retains a good acid balance during ripening. At Geneva, wines have been rated good to excellent. In Arkansas, the better wines have been likened to 'Chardonnay', and lesser quality samples are as good as 'Seyval'. There is some evidence suggestive of potential for sparkling wine production.

Foliage and fruit are moderately susceptible to powdery mildew )*Uncinula necator* [Schw.] Burr.), downy mildew (*Plasmopara viticola* [Berk. and Curt.] Berl. & de Toni) and botrytis bunch rot *Botrytic cinerea* Pers.). Since the foliage is not susceptible to sulfur injury, powdery mildew can be controlled with sulfur applications.

DESCRIPTION OF THE PHOTOGRAPHS

The accompanying photographs show typical specimens of the fruit and leaves of the new variety in color as nearly true as it is reasonably possible to make in a color illustration of this character.

Figure 1A:
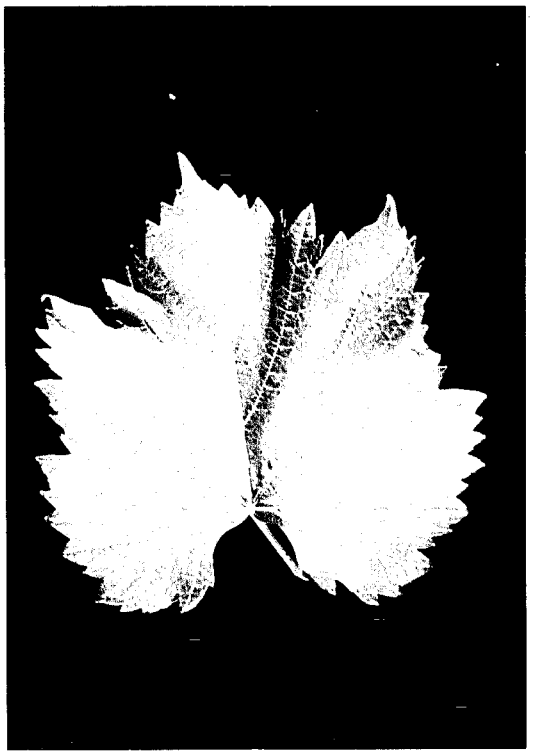
FIG. 1A shows a mature leaf, upper surface.
Figure 1B:
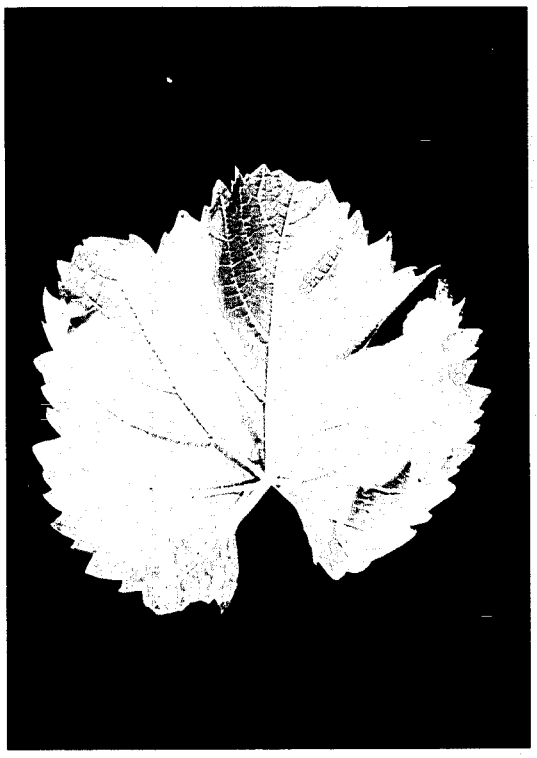
FIG. 1B shows a mature leaf, lower surface.
Figure 2:
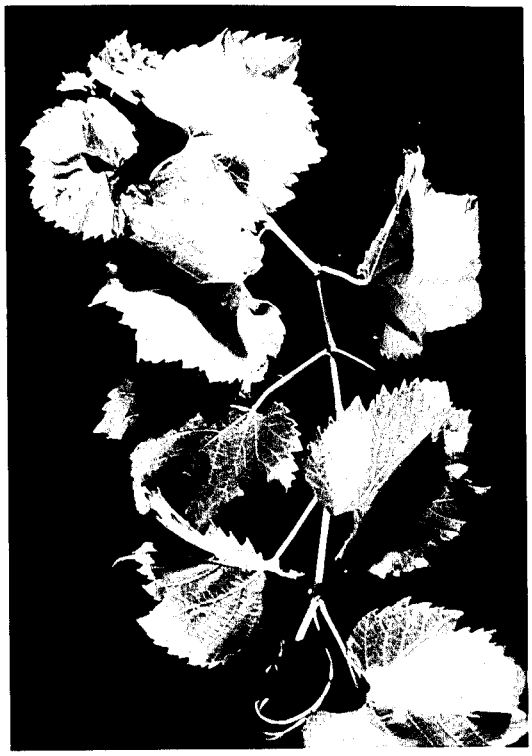
FIG. 2 shows a young shoot.
Figure 3:
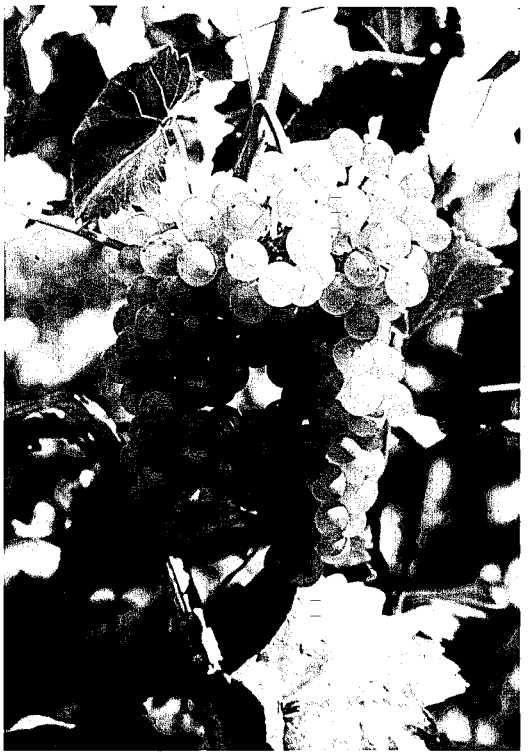
FIG. 3 shows fruit clusters of 'Chardonel'.

The following is a detailed description of the pomological characteristics of the subject grapevine. Color terminology is in accordance with that of The "Royal Horticultural Society Colour Chart" published in 1966 by The Royal Horticultural Society of London, England.

When dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected.

The descriptions reported herein are from specimens grown at Geneva, N.Y.

Vine: Vigorous, with weight of cane prunings/vine/-year between 0.5 and 1.0 kg, upright in growth habit. Bud break follows 'Concord' by several days. The trunk is moderately strong and sheds bark in narrow longitudinal strips. Bark color ranges from brown 200A to block 202A (approximate).

Shoot Tip: Curved with light cobwebby brownish indument. The first flat leaf is glabrous and light green.

Shoot: Inflorescences are borne on nodes 2, 3 and 4 from the base. Very little lateral shoot production occurs. Tendrils are slender and wiry, and discontinuous along the shoot.

Mature leaves: mature leaf shape ranges from cuneiform 146-3-35 to orbicular-reniform 036-3-36. According to the angles formed by the veins (S=131°) the leaf is cuneiform. But according to the raio of leaf length to leaf width (0.73), it tends toward orbicular. The petiolar sinus is lyre-shaped. The leaf margin is entire on most leaves as can be seen from the figures, with occasional leaves having shallow v-shaped sinuses. The upper leaf surface is glabrous, flat, smooth and yellow-green 146B. The lower surface of the leaf is smooth and light grayish-green. Petioles are red 53B with a green 144D background.

Clusters: Shouldered, medium large, averaging 200 g/cluster, usually borne 2 per shoot on primary shoots, Very little crop is found on lateral, secondary and tertiary shoots. Clusters are medium-dense.

Fruit: Medium sized and spherical in shape, fully seeded, maturing in early October in Geneva. The skin is medium-tough, moderately crack-resistant and yellow-green 152D with a light waxy bloom. At Geneva, N.Y., on head-trained, cane pruned vines thinned to one cluster per shoot, the average berry weight is 2.29 grams. The skin adheres tightly to the flesh and the flesh adheres tightly to the seed. There are an average of 2.75 seeds per berry, weighing 42.3 mg per seed. The seed weight accounts for about 5% of the total berry weight. The seeds are pyriform in shape, with a long, prominent beak. The central ridge on the ventral side is prominent, with distinct indentations on either side. On the dorsal side, there is a faint, shallow ridge with a centrally located chalaza. Due to high acidity, low flavor and tough flesh tsxture, the variety has no value in the current table grape market. The flavor of the ripe fruit is mildly fruity, tart, with hints of apricots and apples.

Productivity: Averages 7.1 kg/vine (productive) over three years at Geneva. A metric tonne of fruit yields approximately 535 liters of juice.

Fruit analysis: 10.6° Brix (11 year average), 11.7 g/liter post-fermentation titratable acidity (9 year average) and 2.97 pH (5 year average).

Wine character: Ranks high, produces pleasant and delicate white wine with light fruitiness. In some years, the wine is slightly grassy. Occasinally the wine character is likened to its parent, 'Chardonnay'.

TABLE 3

Isozyme profiles useful in distinguishing 'Chardonel' from other grape cultivars

| | Phosphoglucomutase (PGM) - Rf value: | | | | | |
|---|---|---|---|---|---|---|
| Variety | 0.10 | 0.16 | 0.22 | 0.38 | 0.39 | 0.40 |
| Vignoles | x | | x | | x | x |
| Seyval | x | | x | | x | |
| Chardonel | x | | x | | x | |
| Vidal blanc | x | | x | | x | |
| Cayuga White | x | | | | x | |
| Melody | x | | x | | x | |
| Chardonnay | | | x | x | x | |

Glucose Phosphate Isomerase (GPI) - Rf value

TABLE 3-continued

Isozyme profiles useful in distinguishing 'Chardonel' from other grape cultivars

| Variety | 0.08 | 0.13 | 0.16 | 0.23 | 0.36 | 0.58 |
|---|---|---|---|---|---|---|
| Vignoles | x | x | x | | x | x |
| Seyval | x | | | x | x | x |
| Chardonel | x | x | x | | | x |
| Vidal blanc | x | | | x | x | x |
| Cayuga White | x | | | x | x | x |
| Melody | x | x | x | | | x |
| Chardonnay | x | | x | x | | x |

It is claimed:

1. The new and distinct variety of grape vine herein discribed and illustrated and identified by the characteristics enumerated above.

* * * * *